US009707303B2

(12) United States Patent
Gu et al.

(10) Patent No.: US 9,707,303 B2
(45) Date of Patent: Jul. 18, 2017

(54) REDUCTION STIMULUS-RESPONSIVE GENE DELIVERY SYSTEM AND PREPARATION AND APPLICATION THEREOF

(71) Applicant: SICHUAN UNIVERSITY, Chengdu, Sichuan (CN)

(72) Inventors: Zhongwei Gu, Sichuan (CN); Yu Nie, Sichuan (CN); Yiyan He, Sichuan (CN); Gang Cheng, Sichuan (CN); Li Xie, Sichuan (CN)

(73) Assignee: SICHUAN UNIVERSITY, Chengdu, Sichuan (CN)

( * ) Notice: Subject to any disclaimer, the term of this patent is extended or adjusted under 35 U.S.C. 154(b) by 0 days.

(21) Appl. No.: 14/434,758

(22) PCT Filed: Sep. 29, 2013

(86) PCT No.: PCT/CN2013/084652
§ 371 (c)(1),
(2) Date: Apr. 9, 2015

(87) PCT Pub. No.: WO2014/056414
PCT Pub. Date: Apr. 17, 2014

(65) Prior Publication Data
US 2015/0273080 A1    Oct. 1, 2015

(30) Foreign Application Priority Data
Oct. 10, 2012 (CN) .......................... 2012 1 0380312
Jun. 19, 2013 (CN) .......................... 2013 1 0242451

(51) Int. Cl.
| A61K 48/00 | (2006.01) |
| A61K 47/36 | (2006.01) |
| A61K 47/34 | (2017.01) |
| C12N 15/63 | (2006.01) |
| C12N 15/88 | (2006.01) |
| A61K 47/48 | (2006.01) |

(52) U.S. Cl.
CPC .......... *A61K 48/0041* (2013.01); *A61K 47/34* (2013.01); *A61K 47/36* (2013.01); *A61K 47/48092* (2013.01); *A61K 47/48192* (2013.01); *A61K 48/0091* (2013.01); *C12N 15/63* (2013.01); *C12N 15/88* (2013.01); *C12N 2800/95* (2013.01); *C12N 2810/10* (2013.01)

(58) Field of Classification Search
None
See application file for complete search history.

(56) References Cited

FOREIGN PATENT DOCUMENTS

| CN | 101094652 A | 12/2007 |
| CN | 101265477 A | 9/2008 |
| CN | 101302532 A | 11/2008 |
| CN | 101696272 A | 4/2010 |
| CN | 102899343 A | 1/2013 |

OTHER PUBLICATIONS

Ito et al., Biomaterials 2010, 31(10)2912-2918).*
Meng et al., Biomaterials 2009, 30 (12) 2180-2198.*
Cheng et al., Journal of Controlled Release 2011, 152:2-12.*
Zhixue Xu "A Facile Approach to Construct Hyaluronic Acid Shielding Non-Viral Nano Gene Vector" China Master's Theses Full-text Database Jul. 15, 2011.
Zhixue Xu et al. "Construction of Biomimetic Cross-linking Polyplexes with Thiolated-HA Shielding" Chemical Journal of Chinese Universities, Feb. 2012 vol. 33, No. 2, pp. 404-408.
Hyukjin Lee et al. "Target-specific intracellular delivery of siRNA using degradable hyaluronic acid nanogels" Journal of Controlled Release, 2007 vol. 9, No. 2, pp. 245-252.
Yunus E Kurtoglu et al. "Poly (amidoamine) Dendrimer-Drug Conjugates with Disulfide Linkages for Intracellular Drug Delivery" Biomaterials. Apr. 2009, vol. 30, No. 11, pp. 2112-2121.
Zhongwei Gu et al. "New-generation biomedical materials: peptide dendrimers and their application in biomedicine" Scientia Sinica Chimica, 2010, vol. 40, No. 3, pp. 210-236.
Gang Cheng et al. "Development of a reduction-sensitive diselenide-conjugated oligoethylenimine nanoparticulate system as a gene carrier" International Journal of Nanomedicine, 2012, vol. 7, pp. 3991-4006.
Yiyan He et al. "Polyethyleneimine/DNA polyplexes with reduction-sensitive hyaluronic acid derivatives shielding for targeted gene delivery" Biomaterials 2013, vol. 34, pp. 1235-1245.
Yujiao Yuan et al. "Hyaluronic acid-graft-branch polyethylenimine—a novel vector for siRNA delivery" Journal of Shenyang Pharmaceutical University, Apr. 2012, vol. 29, No. 4, pp. 264-306.
Peisheng Xu et al. "Gene delivery through the use of a hyaluronate-associated intracellularly degradable cross-linked polyethyleneimine" Biomaterials, Oct. 2009, vol. 30, Issue 29, pp. 5834-5843.
Haijun Yu et al. "Influence of the Molecular Weight of Bioreducible Oligoethylenimine Conjugates on the Polyplex Transfection Properties" AAPS Journal, vol. 11, No. 3, Sep. 2009, pp. 445-455.

(Continued)

*Primary Examiner* — Doug Schultz
(74) *Attorney, Agent, or Firm* — Novick, Kim & Lee, PLLC; Allen Xue

(57) ABSTRACT

The present invention discloses a gene delivery system containing a reduction-sensitive shielding system having a targeting function, a preparation method and an application in the field of gene therapy thereof. The gene delivery system is composed of a reduction-sensitive shielding system having a targeting function, cationic polymer material and plasmid DNA; the cationic polymer material and the plasmid DNA complexed to form complex particles, the reduction-sensitive shielding system having a targeting function is shielded on the complex surface by means of electrostatic interaction, so as to reduce the toxicity of the delivery system and successfully transfer the loaded genetic material into cells, thereby achieving expression of genetic material and completing the transfection process, and moreover, improving the targeting and the efficiency of gene transfection.

8 Claims, 6 Drawing Sheets

(56) References Cited

OTHER PUBLICATIONS

Go Saito et al. "Drug delivery strategy utilizing conjugation via reversible disulfide linkages: role and site of cellular reducing activities" Advanced Drug Delivery Reviews, vol. 55, 2003, pp. 199-215.

Periannan Kuppusamy et al, "Noninvasive Imaging of Tumor Redox Status and Its Modification by Tissue Glutathione Levels" Cancer Research, vol. 62, pp. 307-312, Jan. 1, 2002.

\* cited by examiner

US 9,707,303 B2

REDUCTION STIMULUS-RESPONSIVE GENE DELIVERY SYSTEM AND PREPARATION AND APPLICATION THEREOF

FIELD OF THE INVENTION

The present invention relates to the field of biomedical materials, and particularly to a nanoparticle gene carrier.

RELATED ART

Gene therapy has been greatly advanced as a promising therapeutic tool for treating genetic disorders as well as tumors in the past decade. However, the bottleneck for gene therapy is delivery. Nucleic acids are anionic biomacromolecules, thus stable and efficient synthetic carriers are usually positively charged. More and more cationic lipid and polymer delivery systems were developed, which can be electrostatically bound to DNA and used to facilitate gene transfection in vitro.

Among various cationic polymers, polyethylenimine (PEI) has been widely used as the benchmark polymer carrier. However, the inherent cytotoxicity and high positive surface charge of PEI limit its application in vivo. With better understanding of the transfection process of the PEI gene carrier, the PEI/DNA shielding strategy is developed, and various shielding materials have been developed, for example, nonionic hydrophilic polyethylene glycol (PEG), negatively charged liposomes and some biodegradable polymers. These shielding materials may be covalently bound to PEI or be electrostatically bound to PEI/DNA complex, thereby shielding negative charges, lowering the toxicity, preventing aggregation of salt and serum albumin, and even achieving tumor targeting. However, due to strong bonding of these shielding materials to the gene carrier, the shielding materials are not easily released after entering cells, and still tightly wrap the delivered gene, so that the gene cannot exert its effect, thereby greatly reducing the efficiency of gene transfection.

Therefore, it is a technical problem to be solved urgently in the industry to develop a gene delivery system with low-cytotoxicity and high-transfection efficiency.

SUMMARY

The applicants found in research that, in treatment of hereditary diseases and tumors, viruses are the most efficient gene carriers currently, but safety risks that cannot be ignored limit its clinical application of virus carriers. Most viruses are nanoscale particles with a core-shell structure composed of a genome-package core and an outer surrounding enveloper surface protein shell. The characteristic that viruses are stable outside cells, and can recognize the cues provided by cells and undergo stepwise molecular transformations according to changes in vivo or in the microenvironment of the cells, thereby starting a disassembly response provides good inspiration for design of nonviral gene carrier. Chemists have designed a core-shell shaped artificial virus that undergoes "shell deshielding" or "core unpacking" processes like viruses. Such delivery systems are responsive to one specific trigger by enzyme, acid, or reductive reagent, targeting either the tumor extracellular or the intracellular environment, unlike the continuous changes of virus. Dual responsive design also proves that the "artificial viruses" having "shell deshielding" and "core unpacking" are more sensitive, but they do not really imitate the viral programmed responsive deshielding and unpacking process.

Tumor tissues showed at least fourfold concentrations of glutathione (GSH) compared with normal tissues (1~5 µM) (Cancer Research. 2002; 62:307-12.), and the total concentration of GSH was at millimolar (1~10 mM) levels in intracellular compartments (Adv Drug Deliver Rev. 2003; 55:199-215). In view of these findings, a mimic virus gene carrier with dual reduction-sensitive system is designed for programmed gene transfection and targeted killing of tumor cells.

Polyethylenimine (PEI) with a molecular weight of 25 kDa has been widely used as benchmark polymeric vector. However, the inherent cytotoxicity and highly positive surface charge of PEI limit its application in vivo. In contrast, OEI with a molecular weight of 800 Da almost has no cytotoxicity, but cannot effectively compress DNA and has poor transfection ability.

Therefore, the applicant proposed the idea of a gradient-reduction stimulus-responsive gene delivery system for the first time, and expected to develop a stable gene delivery system that can be biodegraded into non-toxic and safe small molecules, and at the same time, has multiple programmed reduction stimulus-responsiveness and high transfection efficiency.

The present invention provides a reduction stimulus-responsive ternary complex nanoparticle gene delivery system and a preparation method thereof, and a gene therapy using the gene delivery system in in vitro gene transfection, tumor, asthma and cardiovascular diseases.

The present invention is achieved through the following technical solutions:

A gene delivery system is provided, which includes a shielding system, cationic polymer material and plasmid DNA. The cationic polymer material and the plasmid DNA are complexed into binary complex particles, the shielding system is shielded on the surface of the binary complex by means of electrostatic interaction to form ternary complex particles, and the shielding system contains a reduction-sensitive bond.

As an optional manner, both of the shielding system and the cationic material contain a reduction-sensitive bond, thus forming a nanoparticle gene carrier having multiple reduction stimulus-response characteristics. The multiple reduction stimulus-response strategy is closer to the deshielding and unpacking processes of viral carrier, can improve the gene delivery efficiency, and is much better than single programmed response.

As an optional manner, the reduction-sensitive bond is at least one of a disulfide bond and a diselenide bond, so the material can be degraded in reductive conditions. Both the shielding system and the cationic material contain a disulfide bond or a diselenide bond, or, one of the shielding system and the cationic material contains a disulfide bond, and the other contains a diselenide bond, or, the shielding system and the cationic material respectively contain a disulfide bond and a diselenide bond at the same time.

As an optional manner, the shielding system contains a disulfide bond, and the cationic material contains a diselenide bond. The gene delivery system having this structure can make a real-time response through changes in chemical structures of molecules under the condition of different extracellular and intracellular reducing agent concentrations of tumors, thereby achieving gradient-reduction stimulus response. As a result, the ternary complex delivery system can be stable in an intracellular low GSH concentration environment and can be cycled for a long period of time, and prevent the DNA from being degraded by deoxyribonuclease (DNase) in the serum; when reaching the target tumor tissue, due to the high GSH concentration in the tumor tissue, the more sensitive disulfide bond in the outer layer (shelter) is first cleaved (or partially cleaved), which is beneficial to endocytosis of the complex particles; after entering the cell, the intracellular GSH concentration is up to 1 to 10 mmol/L which is 1000 folds higher than the extracellular GSH concentration, and at this time, the stable diselenide bond (in the cationic material) is also cleaved, the cationic material is degraded, and DNA is released, which is beneficial to DNA importing into the nuclear, thereby achieving high gene expression.

As an optional manner, the shielding system contains a diselenide bond. The gene delivery system having this structure can protect the DNA, and prevent the DNA from being degraded by deoxyribonuclease (DNase) in the serum, and prevent the negatively charged serum protein in the serum from being coagulated, so as to prevent formation of thrombus. By means of the relatively stable diselenide bond in the outer layer (shelter), the ternary complex delivery system is more stable in the intracellular low GSH concentration environment, can be cycled for a longer period of time, and when reaching the target tumor tissue, under the high GSH concentration in the tumor tissue, the diselenide bond will not be cleaved after a long period of time of contact or after entering the cell; after entering the cell, the entire ternary complex system is completely disassembled, and the DNA is released, thereby achieving gene transfection. A delivery system containing a disulfide bond in the outer layer can be used in combination, so as to achieve better comprehensive effect.

As an optional manner, the shielding system may be a glycosaminoglycan derivative having a reduction-sensitive disulfide bond or diselenide bond and a terminus still being a carboxyl group obtained by modifying the carboxyl group of at least one glucuronic acid unit of glycosaminoglycan. Glycosaminoglycan is one of heteropolysaccharides, and includes: hyaluronic acid, 4-chondroitin sulfate, 6-chondroitin sulfate, dermatan sulfate, heparan sulfate, heparin, keratan sulfate, etc. Glycosaminoglycan is a long-chain polysaccharide formed by repeated disaccharide units, and one of the disaccharide units is hexosamine (glucosamine or galactosamine); and the other one is uronic acid. Glycosaminoglycan is an important part of intercellular substance, and most of the intercellular substance is glycosaminoglycan, so glycosaminoglycan has good biocompatibility and biodegradability.

As an optional manner, the glycosaminoglycan used in the shielding system of the present invention has a molecular weight of 5 to 2000 kDa.

As an optional manner, the glycosaminoglycan in the present invention is at least one of hyaluronic acid, 4-chondroitin sulfate, 6-chondroitin sulfate, dermatan sulfate, heparan sulfate, heparin and keratan sulfate.

As an optional manner, the shielding system is a hyaluronate derivative (HA-SS—COOH) having a reduction-sensitive disulfide bond and a terminus still being a carboxyl group obtained by modifying the carboxyl group of at least one glucuronic acid unit of hyaluronic acid. The schematic structural diagram is as follows:

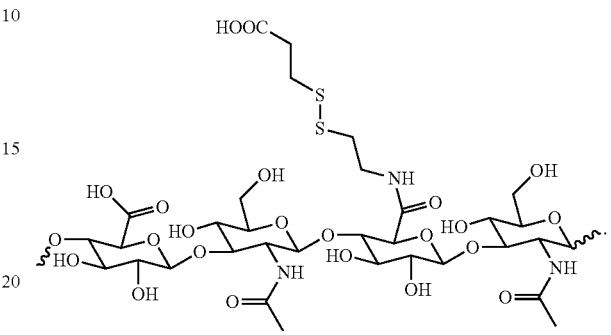

As an optional manner, the cationic material is formed by a disulfide bond- or diselenide bond-containing compound and at least one of polyethylenimine, polypropyleneimine, spermine, amino acid polypeptide, peptides dendrimer and peptides dendrimer-containing cationic lipid material or other lipid materials (such as cationic lipid polymer) through conjugation. The periphery of the cationic material contains rich amino groups, and is easy to conjugate with the disulfide bond- or diselenide bond-containing compound, and the disulfide bond- or diselenide bond-containing compound is disulfide bond- or diselenide bond-containing dicarboxylic acid or diene. The polyethylenimine, polypropyleneimine, spermine, amino acid polypeptide or lipid material has a molecular weight of 200 to 4000 Da.

As an optional manner, the cationic material formed by the disulfide bond- or diselenide bond-containing compound and polyethylenimine or polypropyleneimine or spermine through conjugation has the structural formula below:

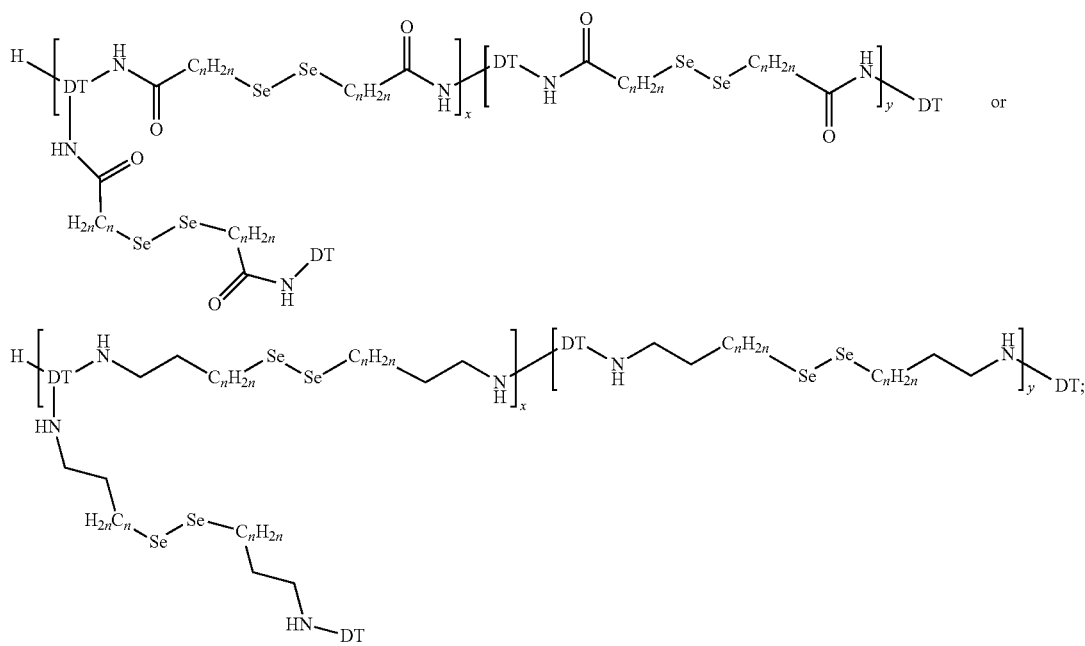

where, n=1 to 10, x≥1, y≥1, and DT is polyethylenimine or polypropyleneimine or spermine. The cationic material has low cytotoxicity, high transfection efficiency, and controllable molecular weight.

As an optional manner, the cationic material is a diselenide-conjugated oligoethylenimine (OEI—SeSex), and the schematic structural diagram is as follows:

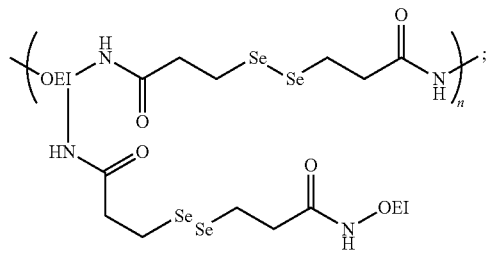

where, n=1 to 10, and x≥1.

As an optional manner, the peptides dendrimer-containing cationic lipid material has the structural formula below:

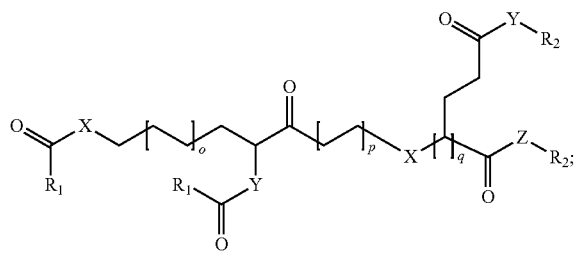

where, R1 is a saturated/unsaturated hydrocarbyl group or an amino group, R2 is an amino group, a saturated/unsaturated hydrocarbyl group or

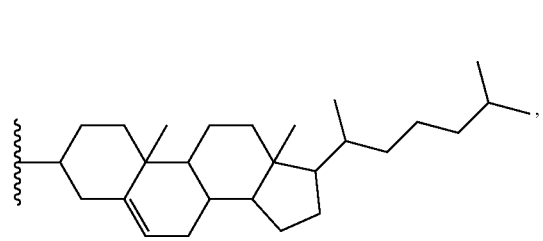 [SMILES: *C1CCC2(C)C(=CCC3C2CCC2(C)C(C(C)CCCC(C)C)CCC32)C1]

at least one of $R_1$ and $R_2$ is an amino group, X, Y, Z is NH, O or S, o, p and q are each independently 1 or 0; the saturated/unsaturated hydrocarbyl group is preferably an alkyl group or an alkenyl group or an aryl group, and is more preferably a C10-C20 alkyl group or alkenyl group or an aryl-containing amino acid derivative, where the amino group is preferably a lysine group or an arginine group or a histamine group.

As an optional manner, the peptides dendrimer-containing cationic lipid material has the structural formula below:

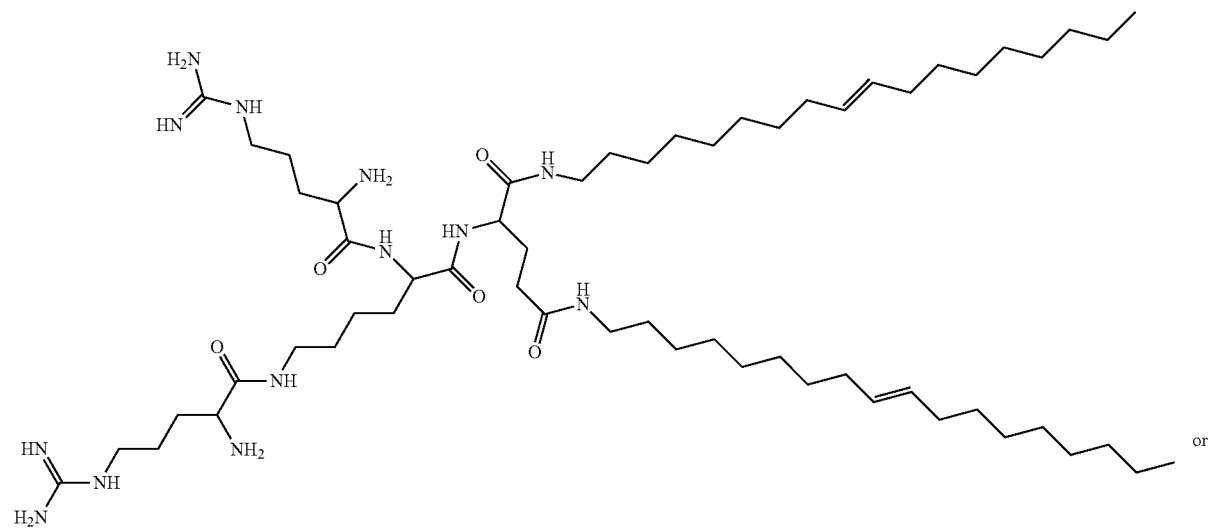

or

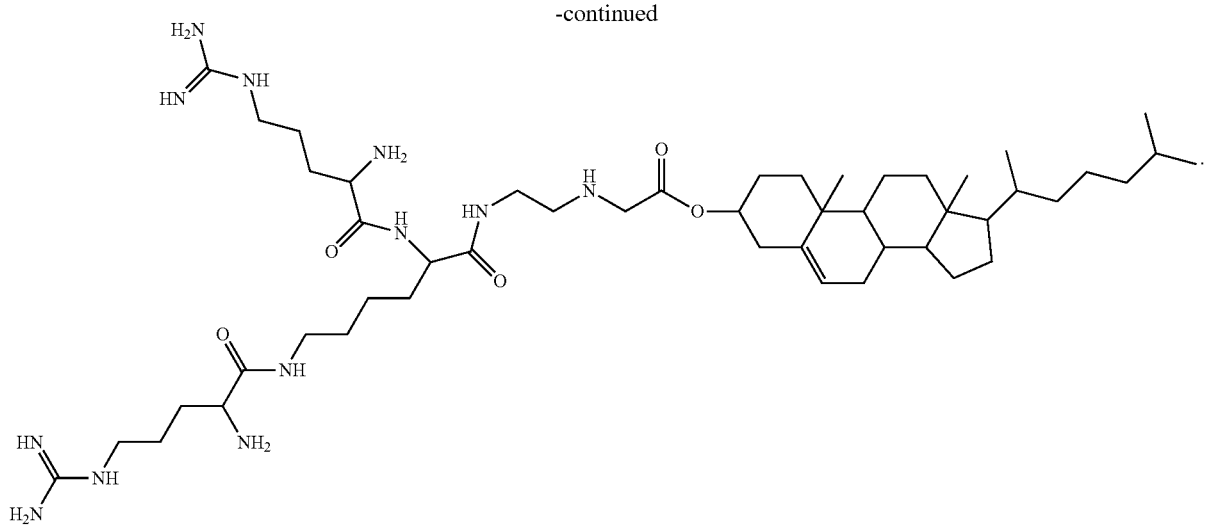

As an optional manner, the plasmid DNA in the gene delivery system of the present invention is eukaryocyte expressed plasmid DNA, and may be recombinant eukaryotic expression plasmid containing reporter gene or cytokine gene or cancer suppressor gene.

As an optional manner, in the gene delivery system of the present invention, the mass ratio of the shielding system to the plasmid DNA is 0.1:1 to 50:1, and the mass ratio of the cationic material to the plasmid DNA is 0.1:1 to 50:1.

The present invention further provides a method for preparing the gene delivery system, which includes the following steps:

dissolving plasmid DNA in sterile water or a sterile HBG buffer (20 mmol 4-hydroxyethyl piperazine-ethanesulfonic acid, 5% glucose) to formulate a DNA solution of a concentration of 0.1 mg/mL; dissolving a cationic material in an HBG buffer to formulate a solution A of a concentration of 0.1 to 10 mg/mL; and dissolving a shielding system in an HBG buffer to formulate a solution B of a concentration of 0.01 to 1 mg/mL; and mixing the solution A obtained in the foregoing step and a DNA solution, and incubating the mixture for 20 min at room temperature to obtain a binary complex, and then adding the solution B, and incubating the mixture for 20 min at room temperature to obtain a ternary complex.

As an optional manner, the method for preparing the gene delivery system includes the following steps:

(1) Preparation of a Reduction-Sensitive Shielding System Having a Targeting Function:

1) dissolving hyaluronic acid in a phosphate buffer (PBS) at pH 6.8, adding 1-(3-dimethylaminopropyl)-3-ethylcarbodiimide hydrochloride (EDC.HCl) and 1-hydroxybenzotriazole (HOBT), stirring, and activating the carboxyl group; and adding cystamine dihydrochloride (Cys) (preferably, a mass ratio of the hyaluronic acid (HA) to the cystamine dihydrochloride is between 1:30 to 30:1), and stirring, reacting for 12 h at room temperature, dialyzing the product after the reaction is completed, and freeze-drying, to obtain cystamine grafted hyaluronic acid (HA-Cys);

2) dissolving cystamine grafted hyaluronic acid (HA-Cys) in phosphate buffer (PBS) at pH 8.5, adding excess amount of dithiothreitol (DTT), reacting for 4 h at room temperature, adjusting the pH value to 3.5 with hydrochloric acid (HCl), adding sodium chloride (NaCl) to a final concentration of 5% (w/v), precipitating with ethanol, re-dissolving in water, and centrifuging and freeze-drying, to obtain thiolated hyaluronic acid (HA-SH);

3) dissolving thiolated hyaluronic acid (HA-SH) in a phosphate buffer (PBS), reacting with excess amount of 3-mercaptopropionic acid overnight at room temperature, after the reaction is completed, dialyzing and freeze-drying the product, to obtain a hyaluronic acid (HA-SS—COOH) with disulfide modification and having a terminus being carboxyl group;

(2) Preparation of a Gene Delivery System Containing the Reduction-Sensitive Shielding System Having a Targeting Function:

dissolving plasmid DNA in sterile water or a sterile HBG buffer, to obtain a DNA solution; dissolving a cationic polymer gene carrier in an HBG buffer, to obtain a solution A; dissolving the reduction-sensitive shielding system having the targeting function (HA-SS—COOH) in an HBG buffer, to obtain a solution B; mixing the DNA solution and the solution B to obtain a complex particles solution of the gene carrier and the plasmid DNA, placing for 20 min at room temperature, and adding the solution B, to obtain the gene delivery system.

The present invention further provides an application of the gene delivery system: combining the gene carrier with a superparamagnetic nanoparticle (MNP) and/or a lipid-soluble drug to prepare a complex carrier or drug for use in in vitro gene transfection and gene therapy of tumors, asthma or cardiovascular diseases, thereby achieving combination of gene therapy and chemotherapy and integration of disease diagnosis and treatment.

The present invention further provides a complex delivery system combining gene carriers and magnetic nanoparticles, where the magnetic nanoparticles may be water soluble or lipid soluble. Preferably, the magnetic nanoparticles and gene are dispersedly distributed in the gene carriers. Preferably, the magnetic nanoparticles are at least one of ferroferric oxide, γ-ferric oxide and manganese, cobalt or zinc-doped iron-oxygen magnetic nanoparticles. Preferably, the magnetic nanoparticles are electronegative, and have an average particle size in the range of 5 to 50 nm and a surface potential in the range of −5 to −50 mV. Preferably, the surface of the magnetic nanoparticles is modified by an electronegative organic material, and the electronegative organic material may be at least one of a carboxyl silane coupling agent, amino acids dendrimer, tartaric acid, citric acid, oxalic acid and acetic acid. By adding the magnetic nanoparticles, the complex delivery system can respond to an external magnetic field, and can be concentrated at the target site under the guidance of the external magnetic field, thereby achieving the magnetic targeting function.

The present invention further provides a complex drug, which includes the gene delivery system and a pharmaceutically active ingredient. The drug and the plasmid DNA can be wrapped in the cationic material, so that the plasmid DNA and the drug can be simultaneously released, so as to achieve the purpose of gene therapy and drug therapy simultaneously; the drug can also be wrapped in the shielding system or wrapped in the shielding system and the cationic material, so that the drug and the DNA can be released at different stages.

The present invention further provides a complex delivery system formed by the gene carrier, a drug and magnetic nanoparticles through complexing. The functions of the three components are integrated in one delivery system.

The present invention further provides an application of the gene carrier, in in vitro gene transfection and gene therapy of tumors, asthma or cardiovascular diseases, thereby achieving combination of gene therapy and chemotherapy and integration of disease diagnosis and treatment.

All features disclosed in this specification or all steps in the method and process disclosed in this specification, except mutually exclusive features and/or steps, can be combined in any manner.

The present invention has the following beneficial effects:

1. In the gene delivery system of the present invention, a hyaluronate derivative is used as the shelter, in one aspect, the complexing capacity of the cationic polymer with DNA will not be influenced, and in another aspect, the binding efficiency of the gene delivery system and a cell surface receptor or by means of the targeting function of hyaluronic acid is improved, and the release ability of endosome is maintained by means of HA receptor-mediated endocytosis, thereby promoting the cellular uptake of the PEI/DNA/HA-SS—COOH ternary complex.

2. For the shielding system of the gene delivery system of the present invention, in one aspect, the carboxyl group on the terminus can be bound with the great amount of amino groups formed on the complex particle surface by the cationic polymer and the plasmid DNA by means of electrostatic interaction, the shielding effect is achieved, the toxicity is lowered, the aggregation caused by serum albumin is avoided, and escape from the scavenging action of the reticuloendothelial system can be achieved, thereby lowering the cytotoxicity of the cationic polymer and increasing the stability of serum; in another aspect, after entering cells, under the action of the intracellular reducing environment, the reduction-sensitive disulfide bond may be cleaved, so that the shielding effect is removed, the loaded gene is exposed, and the escaping ability of the gene from the endosome is improved, thereby significantly improving the transfection efficiency.

3. For the gene delivery system of the present invention, the reduction-sensitive response shielding layer having a targeting function is introduced into the gene carrier by using an electrostatic bonding method; by adjusting the shielding ratio (HA-SS—COOH/DNA), the decrease of the transfection efficiency caused by excessive shielding can be controlled, and at the same time, the specific recognition and transfer of the target tissue by the gene delivery system is improved by using a targeting ligand, and the carried DNA environment is responsively released to the target cell.

4. The multiple reduction stimulus-responsive gene delivery system of the present invention employs a multiple reduction stimulus-response strategy, which is closer to the deshielding and unpacking processes of viral carrier, and the gene transfection efficiency is significantly higher than other conventional single programmed stimulus responsive gene carriers or nonintelligent responsive gene carriers.

5. The diselenide bond-containing reduction stimulus-response cationic material (such as OEI—SeSe$_x$) of the present invention can form nanoscale binary complex particles (OEI—SeSe$_x$/DNA binary polyplexes, abbreviated as DSe) carrying positive charges on the surface with the plasmid DNA through electrostatic interaction. The carboxyl group at the terminus of the disulfide bond-containing reduction stimulus-response shielding system (such as HA-SS—COOH) of the present invention can be combined with the rest positive charges on the DSe surface through electrostatic complexation to form a ternary complex (OEI—SeSe$_x$/DNA/HA-SS—COOH ternary polyplexes, abbreviated as DSeS) having very low positive charges or negative charges on the surface.

6. For the disulfide bond-containing reduction stimulus-response shielding system of the present invention, in one aspect, the effects of shielding positive charges, lowering the toxicity and avoiding the aggregation caused by serum albumin, and escaping from the scavenging action of the reticuloendothelial system can be achieved, thereby lowering the cytotoxicity of the cationic polymer and increasing the stability of serum; in another aspect, after entering cells, under the action of the intracellular reducing environment, more sensitive disulfide bond may be cleaved, so that the shielding effect is removed, the internal DSe is exposed, and the escaping ability of the gene from the endosome is improved, thereby significantly improving the transfection efficiency.

7. The gene delivery system of the present invention can make real-time response through changes in chemical structures of molecules under the condition of different extracellular and intracellular reducing agent concentrations in tumors, thereby achieving gradient-reduction stimulus response. The gradient-reduction stimulus-responsiveness enables the OEI—SeSe$_x$/DNA/HA-SS—COOH ternary complex delivery system to be stable in an intracellular low GSH concentration environment and can be cycled for a long period of time, and prevent the DNA from being degraded by DNase in the serum; when reaching the target tumor tissue, due to the high GSH concentration in the tumor tissue, the more sensitive disulfide bond in the outer layer (shelter) is first cleaved (or partially cleaved), which is beneficial to endocytosis of the complex particles; after entering the cell, the intracellular GSH concentration is up to 1 to 10 mmol/L which is 1000 folds higher than the extracellular GSH concentration, and at this time, the stable diselenide bond (in the cationic material) is also cleaved, the cationic material is degraded, and DNA is released, which is beneficial to DNA importing into the nuclear, thereby achieving high gene expression.

8. The method for preparing the gene delivery system of the present invention is simple to operate and is convenient for mass production.

9. The gene delivery system of the present invention can be conveniently used in in vitro gene transfection and gene therapy of tumors, asthma and cardiovascular diseases.

DETAILED DESCRIPTION

Figure 1:
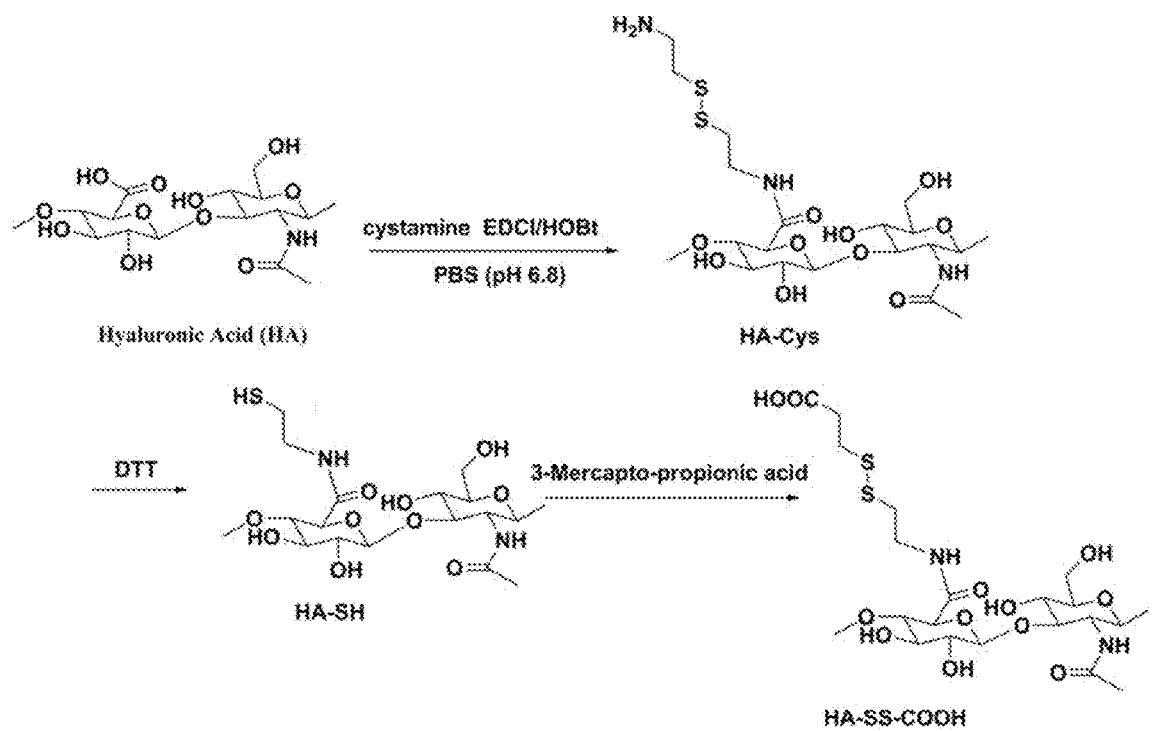
FIG. 1 is a schematic diagram of a structure and a synthesis process of a shielding system of the present invention.

In order to make the objectives, technical solutions and advantages of the present invention clearer and more comprehensible, in the following, the present invention is further illustrated in detail with reference to the accompanying drawings and embodiments. Hyaluronic acid and polyethylenimine used in the following embodiments are exemplary, and those skilled in the art can easily generalize the material to other materials. It should be understood that, the specific embodiments described herein are merely used to explain the present invention, but not intended to limit the present invention.

Acronyms:
DP: Binary complexes of PEI 25 kDa and DNA at a mass ratio of 1.2/1
DSe: Binary complexes of OEI—SeSex and DNA
DPS: Ternary complexes of PEI 25 kDa, DNA and HA-SS—COOH
DSeS: Ternary complexes of OEI—SeSex, DNA and HA-SS—COOH Embodiment 1: Preparation of a Reduction-Sensitive Shielding System Having a Targeting Function According to the feeding proportion in Table 1, the hyaluronic acid was dissolved in phosphate buffer (PBS) at pH 6.8, 1-(3-dimethylaminopropyl)-3-ethylcarbodiimide hydrochloride (EDC.HCl) and 1-hydroxybenzotriazole (HOBT) were added and stirred, and the reactants reacted for 2 h at room temperature to activate the carboxyl group. Cystamine dihydrochloride (Cys) was added and stirred, the reaction solution reacted overnight at room temperature, and after the reaction was completed, the reaction product was dialyzed for 48 h by using a dialysis bag having an interception of 3500, and freeze-dried, to obtain cystamine grafted hyaluronic acid (HA-Cys). The grafting ratio of cystamine in the product (HA-Cys) was calculated according to the NMR spectrum, and the results were shown in Table 1.

Cystamine grafted hyaluronic acid (HA-Cys) of different ratios was dissolved in a phosphate buffer (PBS) at pH 8.5, excess amount of dithiothreitol (DTT) of 5 folds was added, the reactant reacted for 4 h at room temperature, the pH value was adjusted to 3.5 with hydrochloric acid (HCl), and sodium chloride (NaCl) was added to a final concentration of 5% (w/v). Next, the product was precipitated with ethanol, re-dissolved in water, centrifuged and freeze-dried, to obtain thiolated hyaluronic acid (HA-SH). The proportion of SH in the product (HA-SH) was calculated by using the Ellman's assay (see Anal Biochem. 1985; 145: 200-4.), and the results were shown in Table 1.

Thiolated hyaluronic acid (HA-SH) of different proportions was dissolved a phosphate buffer (PBS), and reacted with excess amount of 3-mercaptopropionic acid of 100 folds overnight at room temperature, after the reaction was completed, the reaction product was dialyzed for 48 h by using a dialysis bag having an interception of 3500, and freeze-dried, to obtain a hyaluronate derivative (HA-SS—COOH) with disulfide modification and having a terminus being a carboxyl group. The proportion of S—S in the product (HA-SS—COOH) was calculated by using the Ellman's assay, and the results were shown in Table 1.

TABLE 1

Table of preparation of the reduction-sensitive shielding system having a targeting function

| Product number | HA:EDC•HCl:Cys feeding ratio | Grafting ratio of cystamine in HA-Cys | Proportion of SH in HA-SH | Proportion of S—S in HA-SS—COOH |
|---|---|---|---|---|
| HA-SS—COOH 30 | 10:3.5:10 | 32.9% | 32.5 ± 0.1% | 30.0 ± 0.6% |
| HA-SS—COOH 45 | 10:4.5:10 | 43.4% | 42.7 ± 0.3% | 45.5 ± 0.3% |
| HA-SS—COOH 65 | 10:6.5:10 | 64.7% | 63.0 ± 0.7% | 64.7 ± 0.4% |
| HA-SS—COOH 93 | 1:6.5:30 | 94.4% | 93.9 ± 0.4% | 93.1 ± 0.2% |
| HA-SS—COOH 2 | 30:6.5:1 | 2.2% | 2.2 ± 0.5% | 1.9 ± 0.3% |

In this embodiment, hyaluronic acids having a molecular weight of 5 kDa, 40 kDa, 100 kDa, 1000 kDa and 2000 kDa were respectively used in the preparation test, and the results showed that hyaluronic acid of each molecular weight could be successfully modified, and a hyaluronate derivative with disulfide modification and having a terminus being a carboxyl group was obtained.

Embodiment 2: Preparation of a Gene Delivery System Containing the Reduction-Sensitive Shielding System Having a Targeting Function Plasmid DNA was dissolved in a sterile HBG buffer to formulate a DNA solution A of a concentration of 0.1 mg/mL; the cationic polymer gene carrier polyethylenimine (PEI) was dissolved in a sterile HBG buffer (20 mmol of 4-hydroxyethyl piperazine-ethanesulfonic acid, pH 7.4, 5% glucose) to formulate a PEI solution B of a concentration of 0.01 to 1 mg/mL; and a reduction-sensitive shielding system having a targeting function (HA-SS—COOH) was dissolved in a sterile HBG buffer to formulate an HA-SS—COOH solution C of a concentration of 0.01 to 1 mg/mL.

Cationic polymer PEI solutions of different concentrations and a plasmid DNA aqueous solution were mixed at a mass ratio of 1.2:1, and the mixed aqueous solution was incubated for 20 min at room temperature to obtain a PEI/DNA complex. HA-SS—COOH solutions of different concentrations were added, and the aqueous solution was incubated for 10 min at room temperature, to obtain PEI/DNA/HA-SS—COOH ternary complex in a gene delivery system containing the reduction-sensitive shielding system having a targeting function. The PEI/DNA/HA-SS—COOH ternary complex was used in the subsequent electrophoresis, transfection and toxicity tests. The components and performance of the ternary complex particles prepared according the method were shown in Table 2.

TABLE 2

Components and performance of the PEI/DNA/HA-SS—COOHternarycomplex

| Ternary complex number | Type of HA-SS—COOH | Mass ratio of PEI:DNA:HA-SS—COOH | Particle diameter of ternary complex (nm) | Charge on ternary complex surface (mV) |
|---|---|---|---|---|
| DP | Without a shielding system | 1.2:1 | 116.25 | 27.50 |
| DPS30-0.5 | HA-SS—COOH 30 | 1.2:1:0.5 | 155.20 | 13.97 |
| DPS30-2 | HA-SS—COOH 30 | 1.2:1:2 | 169.30 | 6.72 |
| DPS30-5 | HA-SS—COOH 30 | 1.2:1:5 | 145.20 | −23.40 |
| DPS45-2 | HA-SS—COOH 45 | 1.2:1:2 | 175.54 | 6.71 |
| DPS65-2 | HA-SS—COOH 65 | 1.2:1:2 | 179.12 | 6.77 |
| DPS65-0.1 | HA-SS—COOH 65 | 0.1:1:0.1 | 498.00 | −41.80 |
| DPS65-50 | HA-SS—COOH 65 | 50:1:50 | 150.70 | 23.40 |

In this embodiment, a series of ternary complex particles were successfully prepared by using the hyaluronate derivatives having different molecular weights prepared in Embodiment 1 as the shielding system.

Embodiment 3: Evaluation of the Stability of Complex Particles by Using Gel Electrophoresis 5 µL of a 0.1 mg/mL DNA solution and 3 µL of a 0.2 mg/mL PEI solution were mixed and incubated for 20 min at room temperature, and then 5 µL of HA-SS—COOH solutions of different concentrations were added to HA-SS—COOH/DNA mass ratios of 10, 6, 3, 2, 1 and 0.5 respectively, and the mixture was incubated for 10 min at room temperature. The stability of the complex particles after addition of different amounts of HA-SS—COOH shielding system was detected by a gel retardation assay.

Figure 2:
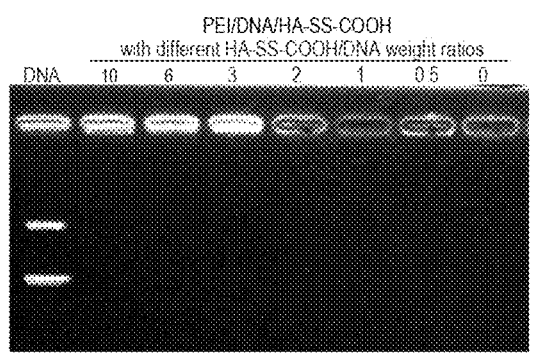
FIG. 2 is an agarose gel electrophoretogram of a PEI/DNA/HA-SS—COOH complex, where there are 8 tracks from left to right, the first track is electrophoretogram of naked DNA, the second to the seventh tracks are electrophoretograms of PEI/DNA/HA-SS—COOH complex when the HA-SS—COOH/DNA mass ratio is 10, 6, 3, 2, 1 and 0.5, and the eighth track is the electrophoretogram of a PEI/DNA complex.

The electrophoresis results in FIG. 2 show that, the complex formed by the cationic polymer and the DNA will not be damaged when the amount of the added HA-SS—COOH hyaluronic acid shielding system reaches 10 folds of the amount of the DNA.

Embodiment 4: Cell Viability Detection

Within 24 h before transfection, B16 cells in the logarithmic growth phase were sampled and diluted with a DMEM medium after trypsinization, seeded in a 96-well culture plate at a density of 1×104 cells per well, and continuously cultured overnight to 80% to 90% cell confuluence in an incubator containing 5% (volume percentage) $CO_2$ at a temperature of 37° C. In transfection, the culture solution injected into the cell culture plate on the previous day was removed through suction, the B16 cells were washed twice with PBS, and then genome transfected complex particles and a DMEM medium containing 10% (mass/volume percentage) calf serum were added to a final volume of 0.1 mL, and continuously cultured for 24 h;

10 µL of an MTT solution (3-(4,5-dimethylthiazole-2)-2,5-diphenyl tetrazolium bromide) of a concentration of 5 mg/mL was added and incubated for 4 h at 37° C., and 150 µL of DMSO (dimethyl sulfoxide) was added. Then, the absorbance value A of each well was detected at a wavelength of 492 nm by using a microplate reader (Bio-Rad). The cell viability was calculated according to the equation below:

Cell viability (%)=($A$sample/$A$control)×100

Asample is the absorbance value of a cell sample well after transfection, and Acontrol is the absorbance value of a cell control well that has not reacted with the transfection complex. The experiment is repeated 6 times for each group.

Figure 3:
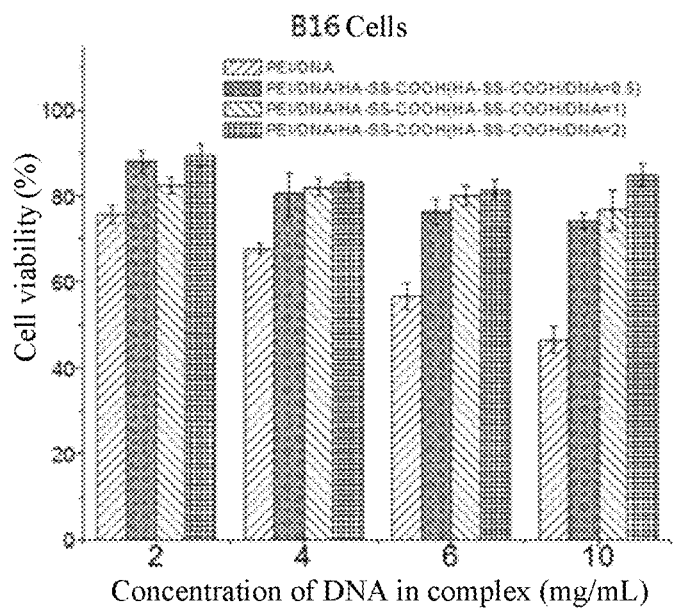
FIG. 3 shows the cell viability at 24 h after transfection of B16 cells by PEI/DNA/HA-SS—COOH complexes of different concentrations.

FIG. 3 shows the cell viability at 24 h after transfection of B16 cells by PEI/DNA/HA-SS—COOH complexes of different concentrations. It can be seen from FIG. 3 that the cytotoxicity on the B16 of the PEI/DNA/HA-SS—COOH ternary complex is much lower than that of the PEI/DNA complex, and the cell viability is 80% ormore, indicating that the gene delivery system of the present invention has low cytotoxicity.

Figure 4:
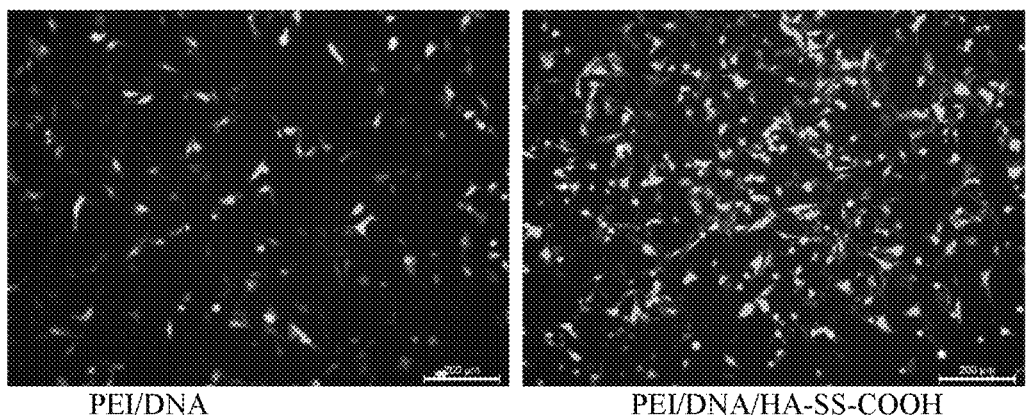
FIG. 4 shows the transfection efficiency of green fluorescent protein plasmid into B16 cells mediated by a PEI/DNA complex and mediated by a PEI/DNA/HA-SS—COOH (HA-SS—COOH/DNA mass ratio of 1) complex.
Figure 5:
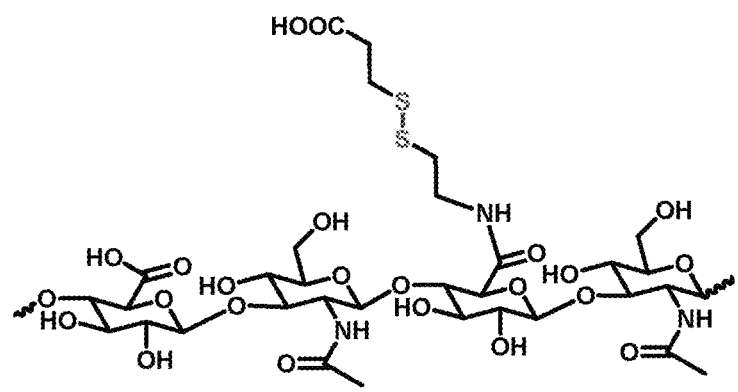
FIG. 5 shows the structural formula of a disulfide bond-containing reduction stimulus-response shielding system of the present invention.
Figure 6:
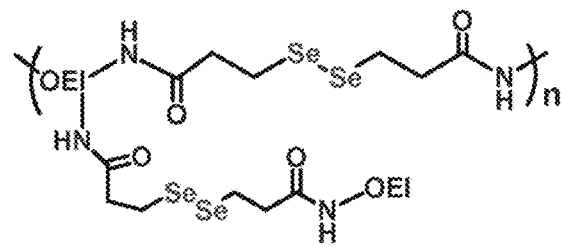
FIG. 6 shows the structural formula of a diselenide bond-containing reduction stimulus-response cationic material of the present invention.
Figure 7:
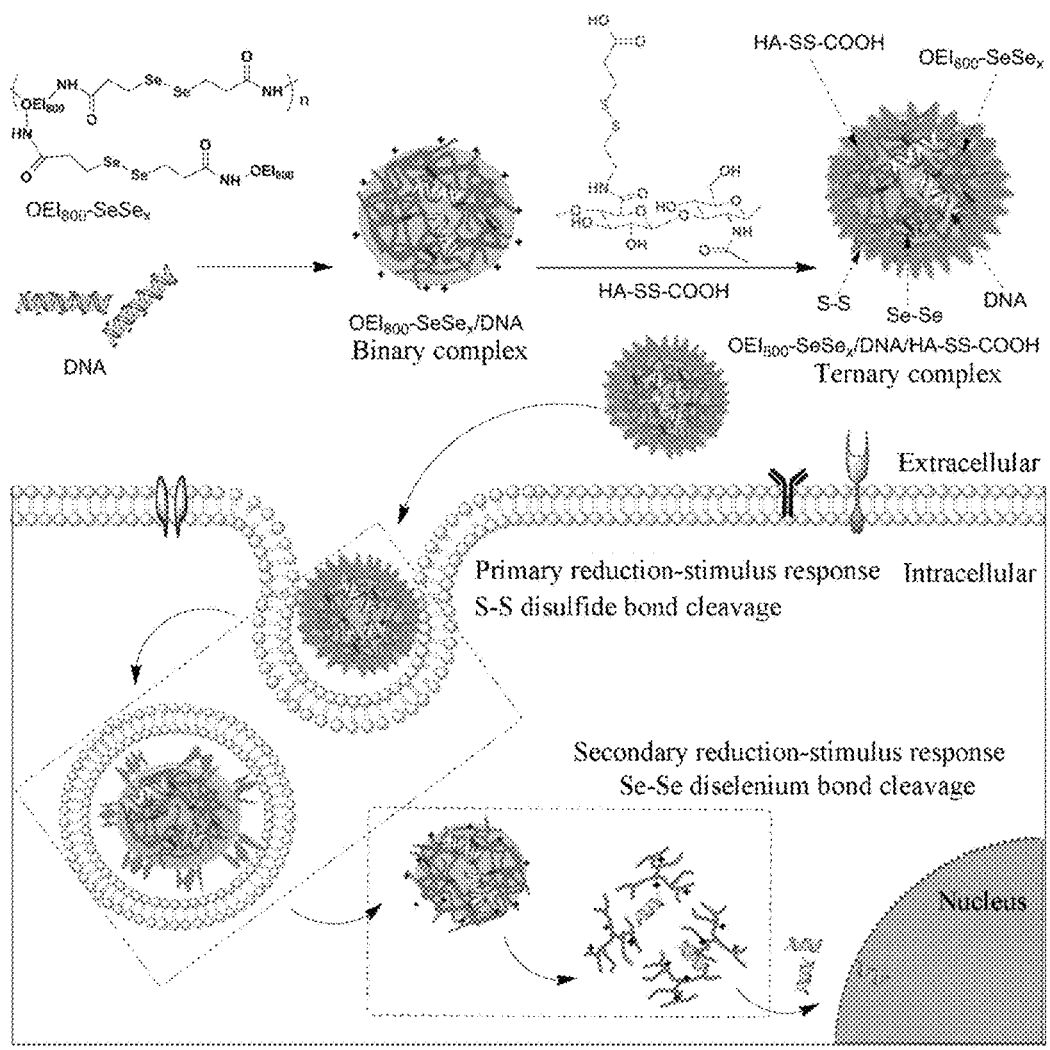
FIG. 7 is a schematic diagram of a ternary complex nanoparticle gene delivery system according to Embodiment 11 of the present invention.

Embodiment 5: Detection of In Vitro Transfection Efficiency of a Green Fluorescent Protein Plasmid into B16 Cells Mediated by a Gene Delivery System Containing a Reduction-Sensitive Shielding System Having a Targeting Function Culture of B16 cells: Murine melanoma cells B16 in a culture solution containing 10% (mass/volume percentage) fetal bovine serum were cultured for 24 h in an incubator containing 5% (volume percentage) $CO_2$ at a temperature of 37° C.;

Before transfection, B16 cells in logarithmic growth phase were diluted with a DMEM medium after trypsinization, seeded in a 6-well culture plate at a density of 4×105 cells per well, and continuously cultured overnight to 80% to 90% cell confuluence in an incubator containing 5% (volume percentage) $CO_2$ at a temperature of 37° C. In transfection, the culture solution injected into the cell culture plate on the previous day was removed through suction, the B16 cells were washed twice with PBS, and then genome transfected complex particles and a DMEM medium containing 10% (mass/volume percentage) calf serum were added to a final volume of 2 mL, and the cells were continuously cultured for 48 h;

Detection of in vitro transfection efficiency: The culture plate was taken out and photographed by an inverted fluorescence microscope; FIG. 4 shows the fluorescent photos of B16 cells transfected by green fluorescent protein plasmid mediated by two gene carriers of PEI/DNA without functional HA-SS—COOH as the shielding system and EI/DNA/HA-SS—COOH having a functional shielding system, respectively. It can be seen from green fluorescent protein expression in the photos that, as the shielding system, HA-SS—COOH significantly improves the expression of the green fluorescent protein plasmid in the B16 cells. HA-SS—COOH has the characteristics of hyaluronic acid (HA), and can interact with receptor CD44 on the B16 cell surface, thus contributing to endocytosis of the PEI/DNA/HA-SS—COOH ternary complex particles; and at the same time, after the particles enter the cell, the reduction-responsive disulfide bond is cleaved, which contributes to release of the shielding system, so that the positive charge of PEI is exposed and exerts the proton pump effect, thereby improving the transfection efficiency.

Embodiment 6: Detection of In Vitro Transfection Efficiency of a Luciferase Plasmid into B16 Cells Mediated by a Gene Delivery System Containing a Reduction-Sensitive Shielding System Having a Targeting Function Culture of B16 cells: B16 cells were cultured by the method the same as that in Embodiment 4.

B16 cells were seeded in a 6-well plate to 4×105 cells/well, and cultured for about 24 h in a cell incubator containing 5% $CO_2$ at 37° C. In transfection, the culture solution injected into the cell culture plate on the previous day was removed through suction, the B16 cells were washed twice with PBS, and then luciferase DNA-containing complex particles listed in Table 3 and a DMEM medium without serum or containing 10%, 50% (mass/volume percentage) calf serum were added to a final volume of 2 mL, and the cells were continuously cultured for 24 h;

Detection of in vitro transfection efficiency: The culture plate was taken out, the culture solution was removed through suction, the cells were washed twice with PBS, and then a lysate containing 1% Triton X-100 was added, and after cell lysis, the cells were detected by using a luciferase assay kit from Promega. The results were shown in Table 4.

According to the present invention, PEI/DNA/HA-SS—COOH ternary complex in a gene delivery system containing a reduction-sensitive shielding system having a targeting function is used to improve the performance of gene carriers, and under the conditions of no serum, containing 10% serum and containing 50% serum, the transfection efficiency in B16 cells is correspondingly increased by 14 folds, 538 folds and 130 folds respectively.

TABLE 3

In vitro transfection efficiency of luciferase plasmid into B16 mediated by a gene delivery system containing a reduction-sensitive shielding system having a targeting function

| Ternary complex number | PEI:DNA:HA-SS—COOH mass ratio | Transfection condition | Transfection efficiency RLU/mg protein |
|---|---|---|---|
| DPS 30 | 1.2:1:1 | no serum | 2.70E+10 |
| DP | 1.2:1 | no serum | 1.87E+09 |
| DPS 30 | 1.2:1:1 | 10% serum | 7.00E+09 |
| DP | 1.2:1 | 10% serum | 1.30E+07 |
| DPS 30 | 1.2:1:1 | 50% serum | 3.88E+08 |
| DP | 1.2:1 | 50% serum | 2.98E+06 |

Embodiment 7: Detection of In Vitro Transfection Efficiency of a Luciferase Plasmid into HepG2 Cells Mediated by a Gene Delivery System Containing a Reduction-Sensitive Shielding System Having a Targeting Function Culture of HepG2 cells: Human liver tumor cells HepG2 in a culture solution containing 10% (mass/volume percentage) fetal bovine serum were cultured for 24 h in an incubator containing 5% (volume percentage) $CO_2$ at a temperature of 37° C.;

HepG2 cells were seeded in a 6-well plate to 4×105 cells/well, and cultured for about 24 h in a cell incubator containing 5% $CO_2$ at 37° C. In transfection, the culture solution injected into the cell culture plate on the previous day was removed through suction, the HepG2 cells were washed twice with PBS, and then luciferase DNA-containing complex particles listed in Table 4 and a DMEM medium without serum or containing 10%, 50% (mass/volume percentage) calf serum were added to a final volume of 2 mL, and the cells were continuously cultured for 24 h;

Detection of in vitro transfection efficiency: The culture plate was taken out, the culture solution was removed through suction, the cells were washed twice with PBS, and then a lysate containing 1% Triton X-100 was added, and after cell lysis, the cells were detected by using a luciferase assay kit from Promega. The results were shown in Table 4.

TABLE 4

In vitro transfection efficiency of luciferase plasmid into HepG2 mediated by a gene delivery system containing a reduction-sensitive shielding system having a targeting function

| Ternary complex number | PEI:DNA:HA-SS—COOH mass ratio | Transfection condition | Transfection efficiency RLU/mg protein |
|---|---|---|---|
| DPS 30 | 1.2:1:1 | no serum | 3.53E+09 |
| DP | 1.2:1 | no serum | 2.74E+08 |
| DPS 30 | 1.2:1:1 | 10% serum | 5.89E+08 |
| DP | 1.2:1 | 10% serum | 2.10E+07 |
| DPS 30 | 1.2:1:1 | 50% serum | 7.93E+07 |
| DP | 1.2:1 | 50% serum | 2.45E+06 |

According to the present invention, PEI/DNA/HA-SS—COOH ternary complex in a gene delivery system containing a reduction-sensitive shielding system having a targeting function is used to improve the performance of gene carriers, and under the conditions of no serum, containing 10% serum and containing 50% serum, the transfection efficiency in HepG2 cells is correspondingly increased by 13 folds, 28 folds and 33 folds respectively.

Embodiment 8: Preparation of a Dual Programmed Reduction Stimulus-Responsive Gene Delivery System (OEI—SS/DNA/HA-SS—COOH)

Plasmid DNA was dissolved in a sterile HBG buffer (20 mmol of 4-hydroxyethyl piperazine-ethanesulfonic acid, 5% glucose) to formulate a DNA solution of a concentration of 0.1 mg/mL; disulfide-conjugated polyethylenimine (OEI—SS) was dissolved in an HBG buffer to formulate an OEI—SS solution of a concentration of 0.1 to 10 mg/mL; and a disulfide bond-containing shielding system (HA-SS—COOH) was dissolved in an HBG buffer to formulate an HA-SS—COOH solution of a concentration of 0.01 to 1 mg/mL.

The OEI—SS solution and the plasmid DNA solution were mixed, and the mixed solution was incubated for 20 min at room temperature to obtain an OEI—SS/DNA binary complex. Then, the HA-SS—COOH solution was added, and the resulting mixed solution was incubated for 20 min at room temperature to obtain OEI—SS/DNA/HA-SS—COOH ternary complex of a disulfide bond-containing multiple programmed reduction stimulus-responsive gene delivery system containing a shielding system and a cationic material.

Embodiment 9: Preparation of Dual Programmed Reduction Stimulus-Responsive Gene Delivery System (OEI—SeSex/DNA/HA-SeSe—COOH)

Plasmid DNA was dissolved in a sterile HBG buffer (20 mmol of 4-hydroxyethyl piperazine-ethanesulfonic acid, 5% glucose) to formulate a DNA solution of a concentration of 0.1 mg/mL; diselenide-conjugated polyethylenimine (OEI—SeSex) was dissolved in an HBG buffer to formulate an OEI—SeSex solution of a concentration of 0.1 to 10 mg/mL; and a diselenide bond-containing shielding system (HA-SeSe—COOH) was dissolved in an HBG buffer to formulate an HA-SeSe—COOH solution of a concentration of 0.01 to 1 mg/mL.

The OEI—SeSex solution and the plasmid DNA solution were mixed, and the mixed solution was incubated for 20 min at room temperature to obtain an OEI—SeSex/DNA binary complex. Then, the HA-SeSe—COOH solution was added, and the resulting mixed solution was incubated for 20 min at room temperature to obtain OEI—SeSex/DNA/HA-SeSe—COOH ternary complex of a diselenide bond-containing multiple programmed reduction stimulus-responsive gene delivery system containing a shielding system and a cationic material.

Embodiment 10: Preparation of Dual Programmed Reduction Stimulus-Responsive Gene Delivery System (OEI—SeSex/DNA/HA-SS—COOH)

Plasmid DNA was dissolved in a sterile HBG buffer (20 mmol of 4-hydroxyethyl piperazine-ethanesulfonic acid, 5% glucose) to formulate a DNA solution of a concentration of 0.1 mg/mL; diselenide-conjugated polyethylenimine (OEI—SeSex) was dissolved in an HBG buffer to formulate an OEI—SeSex solution of a concentration of 0.1 to 10 mg/mL; and a disulfide bond-containing shielding system (HA-SS—COOH) was dissolved in an HBG buffer to formulate an HA-SS—COOH solution of a concentration of 0.01 to 1 mg/mL.

The OEI—SeSex solution and the plasmid DNA solution were mixed, and the mixed solution was incubated for 20 min at room temperature to obtain an OEI—SeSex/DNA binary complex. Then, the HA-SS—COOH solution was added, and the resulting mixed solution was incubated for 20 min at room temperature to obtain a multiple programmed reduction stimulus-responsive gene delivery system OEI—SeSex/DNA/HA-SS—COOH ternary complex.

The in vitro gene transfection test shows that the gene transfection efficiency of the three gene delivery systems in Embodiments 8 to 10 is higher than that of a single programmed reduction stimulus-responsive gene delivery system.

Embodiment 11: Preparation of a Gradient-Reduction Stimulus-Responsive Gene Delivery System Plasmid DNA was dissolved in a sterile HBG buffer (20 mmol of 4-hydroxyethyl piperazine-ethanesulfonic acid, 5% glucose) to formulate a DNA solution of a concentration of 0.1 mg/mL; diselenide-conjugated polyethylenimine (OEI—SeSex) was dissolved in an HBG buffer to formulate an OEI—SeSex solution of a concentration of 0.1 to 10 mg/mL; and a disulfide bond-containing shielding system (HA-SS—COOH) was dissolved in an HBG buffer to formulate an HA-SS—COOH solution of a concentration of 0.01 to 1 mg/mL.

Diselenide-conjugated polyethylenimine (OEI—SeSex) solutions of different concentrations and the plasmid DNA solution were mixed at a certain mass ratio, and the mixed solution was incubated for 20 min at room temperature to obtain an OEI—SeSex/DNA binary complex. Then, HA-SS—COOH solutions of different concentrations were added, the resulting mixed solution was incubated for 20 min at room temperature to obtain a disulfide bond-containing and diselenide bond-containing gradient-reduction dual programmed stimulus-responsive gene delivery system OEI—SeSex/DNA/HA-SS—COOH ternary complex. This OEI—SeSex/DNA/HA-SS—COOH ternary complex was used in the subsequent electrophoresis, transfection and toxicity tests. The components and performance of the ternary complex particles prepared according the method were shown in Table 5.

TABLE 5

Components and performance of the OEI-SeSex/DNA/HA-SS—COOH ternary complex

| Complex abbreviation | Polycation:DNA:HA-SS—COOH mass ratio | Particle diameter of complex(nm) | Charge on complex surface(mV) |
|---|---|---|---|
| DP | 1.2:1:0 | 111.25 | 23.73 |
| DPS | 1.2:1:2 | 197.52 | 6.92 |
| DSe | 0.1:1:0 | >1 μm | −16.12 |
| DSe | 10:1:0 | 84.35 | 27.07 |
| DSe | 50:1:0 | 76.74 | 28.50 |
| DSeS | 10:1:0.1 | 89.43 | 25.65 |
| DSeS | 10:1:2 | 164.50 | 15.54 |
| DSeS | 50:1:50 | >1 μm | −19.48 |

Embodiment 12: Test of Responsiveness of the Diselenide Bond to Reduction Stimulus In order to investigate the responsiveness of the diselenide bond to reduction stimulus, OEI800-SeSex was incubated in GSH (10 μm or 100 μm) of different concentrations for a certain period of time (4 h or 8 h) respectively, and then the molecular weight was determined by gel permeation chromatography (GPC), and chromatogram was shown in FIG. 8. GPC device parameters were as follows: a Waters 2690D HPLC, an ultrahydrogel 120 column and an ultrahydrogel 1000 column connected in series, a refractive index detector; eluent: a 0.1 mol/L sodium formate buffer (pH 2.8), at a flow rate of 1.0 mL/min, at a column temperature of 35° C.; and with polyethylene glycol as standard substance for calculation of molecular weight.

Figure 8:
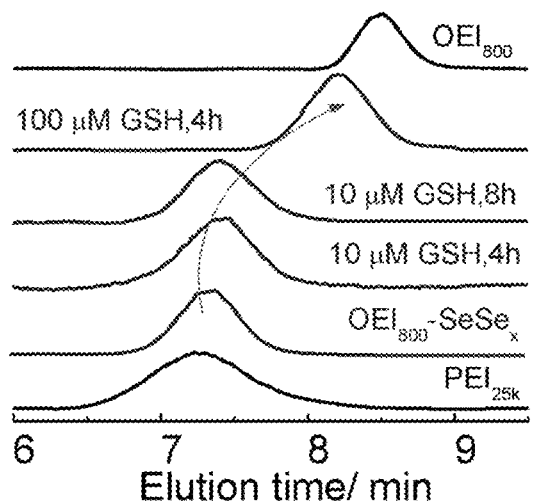
FIG. 8 is a chromatogram detected by GPC.

FIG. 8 is a chromatogram detected by GPC; the curves from bottom to top are: PEI25k polyethylenimine having a molecular weight of 25 kDa; OEI800-SeSex diselenide-conjugated polyethylenimine; OEI800-SeSex after 4 h-treatment with 10 μm GSH; OEI800-SeSex at 8 h-treatment with 10 μm GSH; OEI800-SeSex after 4 h-treatment with 100 μm GSH; and OEI800 oligoethylenimine having a molecular weight of 800 Da, respectively. It can be seen from FIG. 8 that, in this embodiment, OEI800-SeSex having a molecular weight equivalent to that of PEI25k is used, and after 4 h- or 8 h-treatment with 10 μm GSH, the molecular weight is not changed, when after 4 h-treatment with GSH of a higher concentration (100 μm), the molecular weight is reduced to OEI800, indicating that the diselenide bond in OEI800-SeSex is stable in the presence of 10 μm GSH, and will be cleaved in the presence of GSH of a higher concentration of 100 μm, so that OEI800-SeSex is degraded into small-molecule OEI800 fragments. It is reported in literature (Aaps Journal. 2009; 11: 445-455) that the disulfide bond will be cleaved over time in the presence of a reducing agent at the level of 10 μm, indicating that, in the presence of a reducing agent at the same level of 10 μm, the diselenide bond is much stable than the disulfide bond; and in the presence of a reducing agent of a higher level, both the diselenide bond and the disulfide bond will be cleaved. Therefore, the OEI—SeSex/DNA/HA-SS—COOH ternary complex delivery system of the present invention has gradient-reduction stimulus-responsiveness.

Embodiment 13: Cell Viability Assay

Culture of HepG2 cells: Human liver tumor cells HepG2 in a culture solution containing 10% (mass/volume percentage) fetal bovine serum were cultured for 24 h in an incubator containing 5% (volume percentage) $CO_2$ at a temperature of 37° C.

Within 24 h before transfection, HepG2 cells in logarithmic growth phase were diluted with a DMEM medium after trypsinization, seeded in a 96-well culture plate at a density of 1×104 cells per well, and continuously cultured overnight to 80% to 90% cell confuluence in an incubator containing 5% (volume percentage) $CO_2$ at a temperature of 37° C. In transfection, the culture solution injected into the cell culture plate on the previous day was removed through suction, the HepG2 cells were washed twice with PBS, and then transfection complex particles and a DMEM medium containing 10% (mass/volume percentage) fetal bovine serum were added to a final volume of 0.1 mL, and the cells were continuously cultured for 24 h;

Then, 10 μL of an MTT solution (3-(4,5-dimethylthiazole-2)-2,5-diphenyl tetrazolium bromide) of a concentration of 5 mg/mL was added and incubated for 4 h at 37° C., and 150 μL of DMSO (dimethyl sulfoxide) was added. Then, the absorbance value A of each well was detected at a wavelength of 492 nm by using a microplate reader (Bio-Rad). The cell viability was calculated according to the equation below:

Cell viability (%)=($A$sample/$A$control)×100

Asample is the absorbance value of a cell sample well after transfection, and Acontrol is the absorbance value of a cell control well that has not reacted without the transfection complex. The experiment is repeated 6 times for each group.

Figure 9:
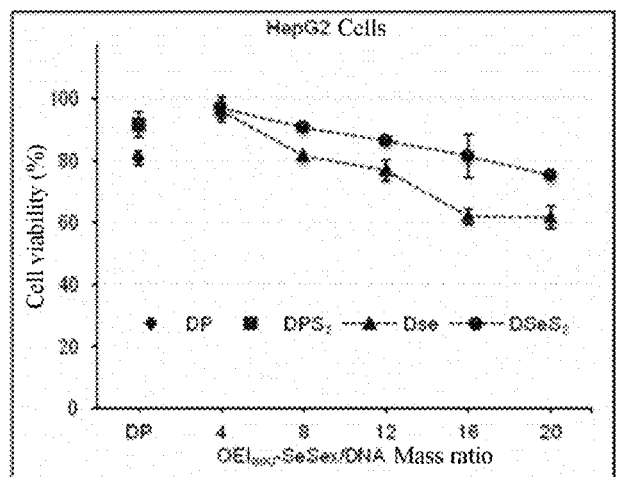
FIG. 9 shows the cell viability at 24 h after transfection in HepG2 cells by different transfection complexes.

FIG. 9 shows the cell viability at 24 h after transfection of HepG2 cells by different transfection complex. It can be seen from FIG. 9 that, the cytotoxicity of the dual programmed stimulus-responsive DSeS ternary complex to HepG2 is much lower than that of the single core stimulus-responsive DSe complex and that of the single shell stimulus-responsive DPS complex, under the condition of the HA-SS—COOH/DNA mass ratio of 2 and different OEI—SeSex/DNA mass ratios, the DSeS cell viability is 80% or more, indicating that the dual programmed stimulus-responsive gene delivery system of the present invention has low cytotoxicity.

Embodiment 14: Detection of In Vitro Transfection Efficiency of Green Fluorescent Protein Plasmid into HepG2 Cells Mediated by Gradient-Reduction Stimulus-Responsive OEI—SeSex/DNA/HA-SS—COOH Ternary Complex Gene Delivery System Before transfection, HepG2 cells in logarithmic growth phase were diluted with a DMEM medium after trypsinization, seeded in a 6-well culture plate at a density of 4×105 cells per well, and continuously cultured overnight to 80% to 90% cell confuluence in an incubatorcontaining 5% (volume percentage) $CO_2$ at a temperature of 37° C. In transfection, the culture solution injected into the cell culture plate on the previous day was removed through suction, the B16 cells were washed twice with PBS, and then transfection complex particles and a DMEM medium containing 10% (mass/volume percentage) fetal bovine serum were added to a final volume of 2 mL, 4 h later, a fresh medium containing 10% fetal bovine serumwas used for replacement, and the cells were continuously cultured for 44 h.

Figure 10:
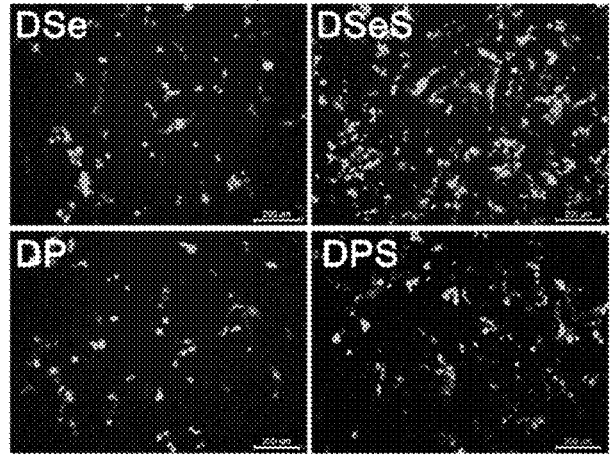
FIG. 10 shows the transfection efficiency of green fluorescent protein plasmid into HepG2 cells mediated by different transfection complexes (DP; DSe; DPS and DSeS)

Determination of in vitro transfection efficiency: The culture plate was taken out and photographed by an inverted fluorescence microscope; FIG. 10 shows the transfection efficiency of green fluorescent protein plasmid into HepG2 cells mediated by different transfection complexes (DP; DSe; DPS; and DSeS), and shows the fluorescent photos of HepG2 cells transfected by green fluorescent protein plasmid mediated by four gene delivery systems of DP as the gene transfection benchmark, single core reduction stimulus-responsive Dse, single shell stimulus-responsive DPS, and dual programmed stimulus-responsive DSeS, respectively.

It can be seen from green fluorescent protein expression in the photos that, the dual programmed gradient-reduction stimulus-responsive DseS gene delivery system significantly improves the expression of the green fluorescent protein plasmid in the HepG2 cells. The disulfide bond-containing HA-SS—COOH serves as the shielding system, and after the particles enter the cell, the reduction-responsive disulfide bond is cleaved, which contributes to release of the shielding system, so that the positive charge of PEI is exposed, exerts the proton pump effect, and helps the particles to escape from the endosome. The further cleavage of the diselenide bond can promote the release of DNA, thereby significantly improving the gene transfection efficiency.

Embodiment 15: Detection of In Vitro Transfection Efficiency of Luciferase Plasmid into HepG2 Cells Mediated by a Gradient-Reduction Stimulus-Responsive OEI—SeSex/DNA/HA-SS—COOH Ternary Complex Gene Delivery System HepG2 cells were seeded in a 6-well plate to 4×105 cells/well, and cultured for about 24 h in a cell incubator containing 5% $CO_2$ at 37° C. In transfection, the culture solution injected into the cell culture plate on the previous day was removed through suction, the HepG2 cells were washed twice with PBS, and then luciferase DNA-containing transfection complex particles listed in Table 2 and a fresh DMEM medium containing 10% (mass/volume percentage) fetal bovine serum were added to a final volume of 2 mL, 4 h later, afresh medium containing 10% fetal bovine serum was used for replacement, and the cells were continuously cultured for 20 h.

Detection of in vitro transfection efficiency: The culture plate was taken out, the culture solution was removed through suction, the cells were washed twice with PBS, and then a lysate containing 1% Triton X-100 was added, after cell lysis, the relative intensity of fluorescence was detected by using a luciferase assay kit from Promega, and the corresponding total protein amount was detected by a BCA kit from Thermo. Finally, the transfection results were expressed as RLU/mg protein, and the results were shown in Table 6.

According to the present invention, by using the gradient-reduction stimulus-responsive OEI—SeSex/DNA/HA-SS—COOH(DSeS*) ternary complex gene delivery system, the gene delivery performance is significantly improved, and the transfection efficiency in HepG2 cells is correspondingly improved by 197.2 folds, 95.4 folds and 43 folds, compared with that of the benchmark DP(*), that of the single core stimulus-responsive DSe(*) and that of the single shell stimulus-responsive DPS(*).

TABLE 6

In vitro transfection efficiency of luciferase plasmid into HepG2 mediated by a gene delivery system containing a reduction-sensitive shielding system having a targeting function

| Complex number | Polycation:DNA:HA-SS—COOH mass ratio | Transfection efficiency RLU/mg protein |
| --- | --- | --- |
| DP (*) | 1.2:1:0 | 2.096E+7 |
| DSe (*) | 10:1:0 | 4.335E+7 |
| DPS (*) | 1.2:1:2 | 9.622E+7 |
| DSeS | 0.1:1:2 | 3.325E+6 |
| DSeS | 50:1:2 | 5.748E+5 |
| DSeS | 10:1:0.1 | 1.165E+9 |
| DSeS (*) | 10:1:2 | 4.137E+9 |
| DSeS | 10:1:50 | 9.918E+4 |

Embodiment 16: Detection of In Vitro Transfection Efficiency of Luciferase Plasmid into HepG2 Cells Mediated by the Ternary Complex Gene Delivery System Containing the Reduction Stimulus-Responsive Glycosaminoglycan Shielding System According to the method in Embodiment 1, the raw material hyaluronic acid was replaced by one glycosaminoglycan of 4-chondroitin sulfate, 6-chondroitin sulfate, dermatan sulfate, heparan sulfate, heparin, and keratan sulfate, to obtain a glycosaminoglycan derivative with disulfide modification having a terminus being a carboxyl group, which was used as the shield system having the reduction-sensitive characteristics.

Plasmid DNA was dissolved in sterile water or a sterile HBG buffer (20 mmol 4-hydroxyethyl piperazine-ethanesulfonic acid, 5% glucose) to formulate a DNA solution of a concentration of 0.1 mg/mL; a cationic material (polyethylenimine, polypropyleneimine, spermine, amino acid polypeptide and lipid were selected for test respectively) was dissolved in an HBG buffer to formulate a solution A of a concentration of 0.1 to 10 mg/mL; the glycosaminoglycan derivative with disulfide modification having a terminus being a carboxyl group was dissolved in an HBG buffer to formulate a solution B of a concentration of 0.01 to 1 mg/mL;

The solution A obtained in the previous step and a DNA solution were mixed, and the mixed solution was incubated for 20 min at room temperature to obtain a binary complex, the solution B was then added, and the mixed solution was incubated for 20 min at room temperature to obtain a ternary complex having the reduction-sensitive characteristics.

The resulting delivery system was used for detection of cell transfection efficiency, (the method was the same as that in Embodiment 7), and a shielding system-free binary complex DP and a non-reduction-sensitive shielding system-containing ternary complex (without disulfide bond modification on glycosaminoglycan) were used as control respectively. The results showed that, the in vitro transfection efficiency of luciferase plasmid into HepG2 cells mediated by a reduction-sensitive glycosaminoglycan derivative other than hyaluronic acid as the shielding system was significantly higher than those of the two control materials, and the results were similar to those in Embodiment 7.

Embodiment 17: Detection of In Vitro Transfection Efficiency of Luciferase Plasmid into HepG2 Cells Mediated by a Reduction Stimulus-Responsive Ternary Complex Gene Delivery System of a Shielding System and a Cationic Material According to the method in Embodiment 1, the raw material hyaluronic acid was replaced by one glycosaminoglycan of 4-chondroitin sulfate, 6-chondroitin sulfate, dermatan sulfate, heparan sulfate, heparin, and keratan sulfate, to obtain a glycosaminoglycan derivative with disulfide modification having a terminus being a carboxyl group, which was used as the shield system having the reduction-sensitive characteristics.

Disulfide bond- or diselenide bond-containing dicarboxylic acid or diene was crosslinked with a cationic material such as polyethylenimine, polypropyleneimine, spermine, amino acid polypeptide or lipid to obtain a reduction-sensitive bond-containing cationic carrier material. The crosslinking may be selected to be a commonly used physical crosslinking or chemical cross-linking method, and for specific method, reference can be made to Chinese Patent Publication No. CN102604130.

Plasmid DNA was dissolved in sterile water or a sterile HBG buffer (20 mmol 4-hydroxyethyl piperazine-ethanesulfonic acid, 5% glucose) to formulate a DNA solution of a concentration of 0.1 mg/mL; the reduction-sensitive cationic material was dissolved in an HBG buffer to formulate a solution A of a concentration of 0.1 to 10 mg/mL; the reduction-sensitive shielding system was dissolved in an HBG buffer to formulate a solution B of a concentration of 0.01 to 1 mg/mL;

The solution A obtained in the previous step and a DNA solution were mixed, and the mixed solution was incubated for 20 min at room temperature to obtain a binary complex, the solution B was then added, and the mixed solution was incubated for 20 min at room temperature to obtain a ternary complex having the multiple programmed reduction-sensitive characteristics.

The resulting delivery system was used for detection of cell transfection efficiency, (the method was the same as that in Embodiment 15) and a shielding system-free binary complex DP and a non-reduction-sensitive ternary complex (without disulfide bond modification on glycosaminoglycan and the cationic material) were used as control respectively. The results showed that, the in vitro transfection efficiency of luciferase plasmid into HepG2 cells mediated by a reduction-sensitive glycosaminoglycan derivative other than hyaluronic acid as the shielding system was significantly higher than those of the two control materials, and is much higher than that of the gene delivery having the single programmed reduction-sensitive characteristics prepared in Embodiment 16, and the results were similar to those in Embodiment 15.

Embodiment 18: Preparation of Complex Delivery System and Detection of In Vitro Transfection Efficiency of Luciferase Plasmid into HepG2 Cells Mediated by the Complex Delivery System A therapeutic plasmid DNA was dissolved in a sterile HBG buffer to formulate a DNA solution of a concentration of 0.1 mg/mL; disulfide bond- or diselenide bond-containing dicarboxylic acid or diene was crosslinked with a cationic material such as polyethylenimine, polypropyleneimine, spermine, amino acid polypeptide or lipid to obtain a reduction-sensitive bond-containing cationic carrier material, which was dissolved in an HBG buffer to formulate a solution A of a concentration of 0.1 to 10 mg/mL; a glycosaminoglycan derivative shielding system with disulfide modification and having a terminus being a carboxyl group was dissolved in an HBG buffer to formulate a solution B of a concentration of 0.01 to 1 mg/mL.

The disulfide and a plasmid DNA solution were mixed, and at the same time, magnetic nanoparticles were added. The mixed solution was incubated for 20 min at room temperature to obtain a cationic material/DNA/magnetic nanoparticle ternary complex. Then, the solution B was added (in this step, the magnetic nanoparticles might be added again), and the resulting mixed solution was incubated for 20 min at room temperature to obtain a complex delivery system combined with the magnetic nanoparticles. The complex delivery system combined with magnetic nanoparticles could respond to an applied magnetic field. Or, the solution A and a plasmid DNA solution were mixed, and at the same time, a drug was added. The mixed solution was incubated for 20 min at room temperature to obtain a cationic material/DNA/drug ternary complex. Then, the solution B was added (in this step, the drug might be added again), and the resulting mixed solution was incubated for 20 min at room temperature to obtain a complex delivery system combined with the drug.

Or, the solution A and a plasmid DNA solution were mixed, and the mixed solution was incubated for 20 min at room temperature to obtain a cationic material/DNA binary complex. Then, the solution B was added, and at the same time, a drug was added. The resulting mixed solution was incubated for 20 min at room temperature to obtain another complex delivery system combined with the drug.

Magnetic nanoparticles and a drug might also be added together during the preparation of the gene delivery system to obtain a complex delivery system combined with the magnetic nanoparticle and the drug. The complex delivery system combined with the magnetic nanoparticle and the drug could respond to an applied magnetic field.

Figure 11:
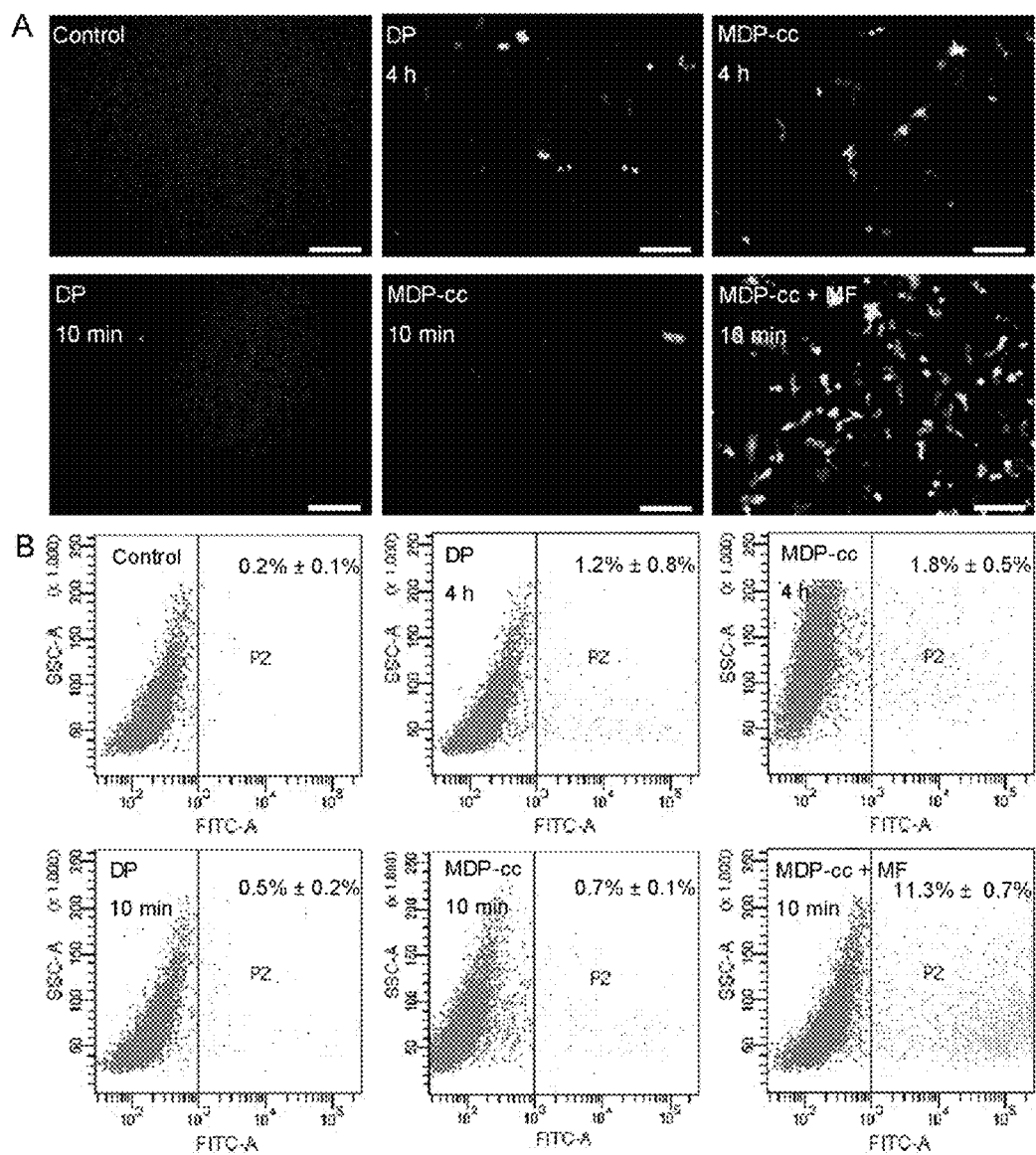
FIG. 11 shows the transfection efficiency of green fluorescent protein plasmid into HepG2 cells mediated by different transfection complexes (control: HepG2 cells without transfection, DP: a polycation/DNA/shelter ternary complex of the present invention, MDP-cc: a polycation/DNA/shelter+MNP quaternary complex of the present invention, MF represents placing a magnet below the culture plate after transfection) according to Embodiment 18, where A is a fluorescence microphotograph, B is the detection result of a flow cytometry.

During preparation of the gene delivery systems in the embodiments, when mixing the solutions of DNA, the cationic material and the shielding system, magnetic nanoparticle and/or a corresponding drug (such as doxorubicin, paclitaxel, 5-fluorouracil, methotrexate and cisplatin) was added to prepare a multifunctional gene delivery system having reduction-sensitive characteristics and magnetic responsiveness, or a gene delivery system having reduction-sensitive characteristics and drug therapy, or a gene delivery system having the three characteristics. In vitro gene transfection results showed that: the gene transfection efficiency of the multifunctional gene delivery system was equivalent to that of a delivery system without magnetic nanoparticles and/or a corresponding drug, and it should be noted that: the magnetic nanoparticle-containing multifunctional delivery system could achieve high transfection efficiency under the supporting effect of an applied magnetic field (by placing a magnet below the culture plate). The promotion effect of magnetic nanoparticles and an applied magnetic field on gene transfection was also detected by using a flow cytometry. FIG. 11 shows the comparison results through fluorescent photomicrographs and detection results of the flow cytometry, where A is fluorescence microphotograph (bright spots are successfully transfected cells), B is the detection results of the flow cytometry, the control group is HepG2 cells without transfection, DP group is HepG2 cells transfected by the polycation/DNA/shelter ternary complex of the present invention, MDP-cc group is HepG2 cells transfected by the polycation/DNA/shelter+MNP quaternary complex of the present invention, and MF represents placing a magnet below the culture plate after transfection. The results of the two detection methods are substantially the same: at 10 min after transfection, the transfection efficiency of the magnetic nanoparticle-containing group is improved, compared with that of the magnetic nanoparticle-free group, at 4 h after transfection, the improvement is significantly, and under the effect of an applied magnetic field, the transfection efficiency at 10 min after transfection is significantly higher than those of all other experimental groups.

Example 19: In Vivo Therapeutic Effect of Complex Delivery System

Building mouse tumor models: HepG2 cells in logarithmic growth phase and good growth state were digested with 0.25% trypsase, to which a PBS buffer was added to formulate a single cell suspension, and 2×106 cells were subcutaneously inoculated at the right side of the lower back of the mouse at an inoculation volume of 50 µL. One week after inoculation, 42 mice with tumor of similar volume of about 100 mm3 were selected as the experimental models (with two being standby mice).

The mice were randomly divided into 5 groups, 8 mice in each group:

A group: regular tail vein injection with phosphate buffer (PBS);

B group: regular tail vein injection with the polycation/DNA/shelter ternary complex solution of the present invention;

C group: regular tail vein injection with the polycation/DNA/shelter+MNP quaternary complex solution of the present invention;

D group: regular tail vein injection with the polycation/DNA/shelter+doxorubicin quaternary complex solution of the present invention; and E group: regular tail vein injection with the polycation/DNA/shelter+doxorubicin+MNP quinary complex solution of the present invention.

Figure 12:
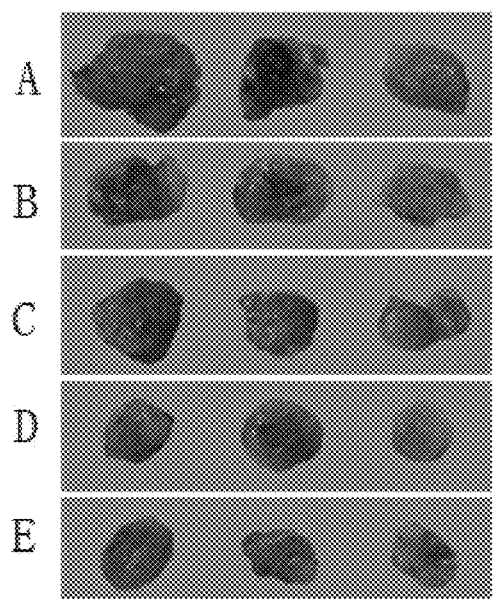
FIG. 12 shows photos of tumor tissues of each group after 21-day in vivo treatment according to Embodiment 19, each group having 3 parallel samples.
Figure 13:
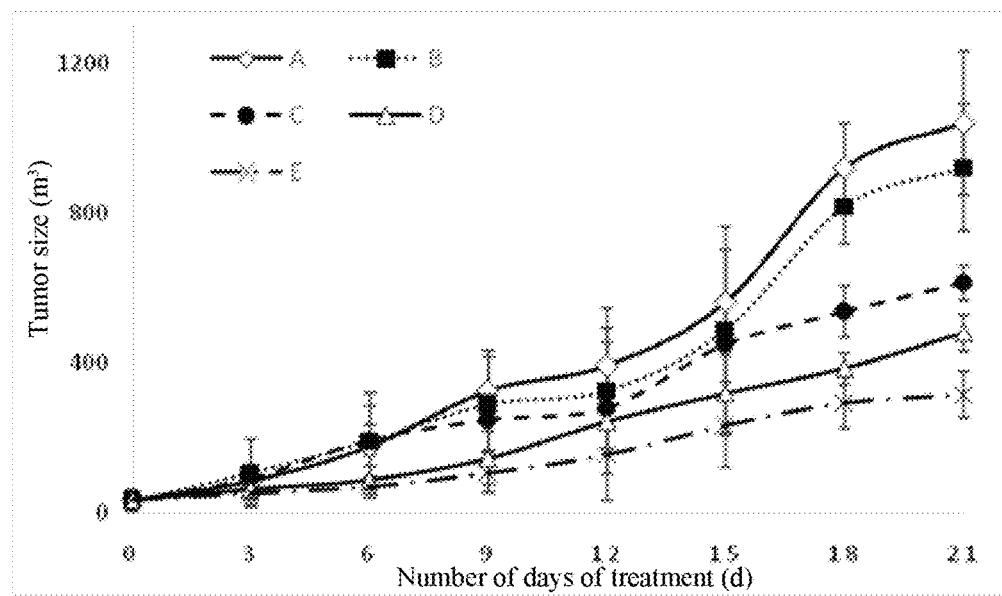
FIG. 13 shows statistical results of the volume of tumor taken out at different time points in the in vivo treatment experiment according to Embodiment 19 (each group having 8 parallel samples at each time point).

The injection was carried out once every three days, the tumor size was measured at 0, 3, 6, 9, 12, 15, 18, 21 day by using a vernier caliper (8 parallel samples were taken at each time point for each group), and the mice were sacrificed at 21 day, the tumor was taken out and photographed (3 parallel samples were taken for each group), and the results were as shown in FIG. 12 and FIG. 13. It can be seen from FIG. 12 and FIG. 13 that, compared with the PBS group, the materials of the B, C, D and E groups has significant inhibition effect on the increase of tumor size, and the inhibition effects on the increase of tumor size of the materials of the groups were sorted in an ascending order: E group>D group>C group>B group>A group.

The invention claimed is:

1. A reduction stimulus-responsive gene delivery system, comprising a shielding system, a cationic polymer material and plasmid DNA, wherein:
    the cationic polymer material and the plasmid DNA are complexed to form binary complex particles,
    the shielding system comprises a disulfide bond, and the cationic material comprises a diselenide bond,
    the shielding system bonds to the surface of the binary complex by means of electrostatic interaction to form ternary complex particles, and
    the shielding system comprises a glycosaminoglycan derivative having a reduction-sensitive disulfide bond and at least one modified glucuronic acid unit, the at least one modified glucuronic acid unit comprising a moiety containing a carboxyl group linked via said reduction-sensitive disulfide bond.

2. The gene delivery system according to claim 1, wherein the cationic material is at least one of diselenide-conjugated polyethylenimine, polypropyleneimine, spermine, amino acid polypeptide, peptides dendrimer and a peptides dendrimer-containing cationic lipid material.

3. The gene delivery system according to claim 1, wherein the shielding system comprises a hyaluronic acid derivative having a reduction-sensitive disulfide bond and at least one modified glucuronic acid unit, the at least one modified glucuronic acid unit comprising a moiety containing a carboxyl group linked via said reduction-sensitive disulfide bond.

4. The gene delivery system according to claim 1, wherein the cationic material is a diselenide-conjugated oligoethylenimine (OEI-SeSex).

5. A method for preparing the gene delivery system according to claim 1, comprising:
   1) dissolving plasmid DNA in sterile water or a sterile HBG buffer (20 mmol 4-hydroxyethyl piperazine-ethanesulfonic acid, 5% glucose) to formulate a DNA solution of a concentration of 0.1 mg/mL; dissolving a cationic material in an HBG buffer to formulate a solution A of a concentration of 0.1 to 10 mg/mL; and dissolving a shielding system in an HBG buffer to formulate a solution B of a concentration of 0.01 to 1 mg/mL; and
   2) mixing the solution A obtained in step 1) and a DNA solution, and incubating the mixture for 20 min at room temperature to obtain a binary complex, and then adding the solution B, and incubating the mixture for 20 min at room temperature to obtain a ternary complex.

6. A method for preparing the gene delivery system according to claim 5, comprising:
   (1) preparation of a reduction-sensitive shielding system having a targeting function:
   1) dissolving hyaluronic acid in a phosphate buffer (PBS) at pH 6.8, adding 1-(3-dimethylaminopropyl)-3-ethyl-carbodiimide hydrochloride (EDC.HCl) and 1-hydroxybenzotriazole (HOBT), stirring, and activating the carboxyl group; and adding cystamine dihydrochloride (Cys), and stirring, reacting for 12 h at room temperature, dialyzing the product after the reaction is completed, and freeze-drying, to obtain cystamine grafted hyaluronic acid (HA-Cys);
   2) dissolving cystamine grafted hyaluronic acid (HA-Cys) in a phosphate buffer (PBS) of pH 8.5, adding excess amount of dithiothreitol (DTT), reacting for 4 h at room temperature, adjusting the pH value to 3.5 with hydrochloric acid (HCl), adding sodium chloride (NaCl) to a final concentration of 5% (w/v), precipitating with ethanol, and re-dissolving in water, and centrifuging and freeze-drying, to obtain thiolated hyaluronic acid (HA-SH); and
   3) dissolving thiolated hyaluronic acid (HA-SH) in a phosphate buffer (PBS), reacting with excess amount of 3-mercaptopropionic acid overnight at room temperature, after the reaction is completed, dialyzing and freeze-drying the product, to obtain a hyaluronic acid (HA-SS—COOH) with disulfide modification and having a terminus being carboxyl group;
   (2) preparation of a gene delivery system containing the reduction-sensitive shielding system having a targeting function:
   Dissolving plasmid DNA in sterile water or a sterile HBG buffer, to obtain a DNA solution; dissolving a cationic polymer gene carrier in an HBG buffer, to obtain a solution A; dissolving the reduction-sensitive shielding system having the targeting function (HA-SS—COOH) in an HBG buffer, to obtain a solution B; mixing the DNA solution and the solution B to obtain a complex particles solution of the gene carrier and the plasmid DNA, placing for 20 min at room temperature, and adding the solution B, to obtain the gene delivery system.

7. A complex delivery system, formed by complexing the gene delivery system according to claim 1 and magnetic nanoparticles and/or a pharmaceutically active ingredient.

8. The gene delivery system according to claim 1, wherein the shielding system comprises a hyaluronic acid derivative having the following structure:

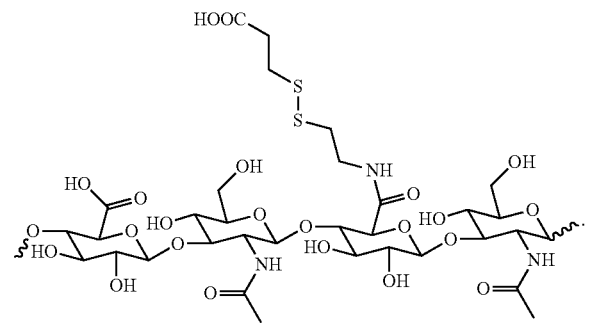

* * * * *